(12) United States Patent
Iwamori et al.

(10) Patent No.: US 8,313,826 B2
(45) Date of Patent: Nov. 20, 2012

(54) MEDICAL INSTRUMENTS

(75) Inventors: Satoru Iwamori, Ishikawa (JP); Hiraku Murayama, Shizuoka (JP)

(73) Assignee: Termo Kabushiki Kaisha, Shibuya-Ku, Tokyo (JP)

( * ) Notice: Subject to any disclaimer, the term of this patent is extended or adjusted under 35 U.S.C. 154(b) by 1143 days.

(21) Appl. No.: 11/887,897

(22) PCT Filed: Mar. 31, 2006

(86) PCT No.: PCT/JP2006/306801
§ 371 (c)(1),
(2), (4) Date: Nov. 9, 2007

(87) PCT Pub. No.: WO2006/109590
PCT Pub. Date: Oct. 19, 2006

(65) Prior Publication Data
US 2009/0053527 A1   Feb. 26, 2009

(30) Foreign Application Priority Data

Apr. 5, 2005 (JP) .................. 2005-108395
Jan. 18, 2006 (JP) .................. 2006-009722

(51) Int. Cl.
*B32B 7/00* (2006.01)
*B32B 15/08* (2006.01)
*B32B 15/18* (2006.01)
*B32B 27/08* (2006.01)
*B32B 27/16* (2006.01)
*B32B 27/28* (2006.01)
*B32B 37/06* (2006.01)

(52) U.S. Cl. ........ 428/212; 428/421; 428/422; 428/457; 428/461; 428/500; 428/515; 428/520; 428/522; 427/314; 427/316; 427/318; 427/248.1; 427/255.6; 427/372.2; 427/375; 427/384; 427/385.5; 427/402; 427/409; 427/412.1; 427/412.4; 427/407.1

(58) Field of Classification Search ........................ None
See application file for complete search history.

(56) References Cited

U.S. PATENT DOCUMENTS 5,079,093 A * 1/1992 Akashi et al. .............. 428/411.1
5,443,455 A   8/1995 Hergenrother et al.
(Continued)

FOREIGN PATENT DOCUMENTS

JP   5-168695 A   7/1993
(Continued)

OTHER PUBLICATIONS

International Preliminary Report on Patentability PCT/IB/338 dated Oct. 18, 2007 for International Appliction No. PCT/JP2006/306801.

*Primary Examiner* — Vivian Chen
(74) *Attorney, Agent, or Firm* — Buchanan Ingersoll & Rooney PC

(57) ABSTRACT

By coating a base material with a film of a fluoropolymer such as PTFE, the coefficient of friction of the base material is lowered and the slipperiness of the base material is thus improved. Thus, it is intended to provide a medical instrument, for example, a guide wire for introducing a catheter. A medical instrument which has, on at least a part of a base material, a hydrophilic polymer film and a fluoropolymer film located as the upper layer thereof.

17 Claims, 2 Drawing Sheets

U.S. PATENT DOCUMENTS

| | | | |
|---|---|---|---|
| 5,670,558 A | 9/1997 | Onishi et al. | |
| 5,849,368 A * | 12/1998 | Hostettler et al. | 427/536 |
| 5,888,591 A * | 3/1999 | Gleason et al. | 427/522 |
| 5,919,570 A * | 7/1999 | Hostettler et al. | 428/424.8 |
| 6,048,620 A * | 4/2000 | Zhong | 428/424.4 |
| 6,168,801 B1 * | 1/2001 | Heil et al. | 424/426 |
| 6,335,029 B1 | 1/2002 | Kamath et al. | |
| 6,753,071 B1 * | 6/2004 | Pacetti | 428/212 |
| 6,926,919 B1 * | 8/2005 | Hossainy et al. | 427/2.25 |
| 7,014,913 B2 * | 3/2006 | Pacetti | 428/212 |
| 7,056,550 B2 * | 6/2006 | Davila et al. | 427/2.24 |
| 7,247,313 B2 * | 7/2007 | Roorda et al. | 424/423 |
| 7,396,539 B1 * | 7/2008 | Hossainy et al. | 424/423 |
| 7,476,246 B2 * | 1/2009 | Pathak | 623/1.46 |
| 2002/0172829 A1 * | 11/2002 | Mori et al. | 428/407 |
| 2005/0033417 A1 * | 2/2005 | Borges et al. | 623/1.46 |
| 2006/0085080 A1 | 4/2006 | Bechgaard et al. | |

FOREIGN PATENT DOCUMENTS

| | | |
|---|---|---|
| JP | 8-24328 A | 1/1996 |
| JP | 8-501262 A | 2/1996 |
| JP | 2001-238963 A | 9/2001 |
| JP | 2002-28249 A | 1/2002 |
| JP | 2002-028249 A | 1/2002 |
| JP | 2002-531183 | 9/2002 |
| JP | 2004-181089 A | 7/2004 |
| JP | 2004-298269 A | 10/2004 |
| WO | WO 98/38258 A1 | 9/1998 |
| WO | WO 2004/032987 A1 | 4/2004 |

\* cited by examiner

MEDICAL INSTRUMENTS

TECHNICAL FIELD

The present invention relates to medical instruments such as a guide wire that comprise a substrate on which is formed a polytetrafluoroethylene (PTFE) or otherwise fluorine-based thin film to provide high adhesion and which excel in slipperiness.

BACKGROUND ART

Fluororesin films have such properties that they excel not only in resistance to strong acids, strong alkalis and organic solvents but also in heat resistance and that they have extremely small friction coefficients to exhibit good slipperiness; in particular, tetrafluororesins typified by polytetrafluoroethylene (hereinafter abbreviated as PTFE) excel in thermal and chemical stability and friction characteristics (with slipperiness being particularly good), as well as excel in biocompatibility; hence, they are applied in various fields of medical equipment.

Patent Document 1 describes a guide wire comprising dissimilar metals welded together to form a wire body, with the weld joint being covered with a coating layer that is formed of a fluoropolymer.

However, PTFE, because it excels in thermal and chemical characteristics, has only poor thermal fusing and bonding properties and, particularly in the case of bonding to metals, it is subjected to a special surface treatment; take, for example, the case of applying a PTFE coating to provide improved friction characteristics; in one of two special methods currently adopted, the surface of PTFE is activated by defluorination with a metallic sodium/liquid ammonia solution and bonded with an epoxy adhesive; in the alternative method, a tetrafluoroethylene/hexafluoropropylene copolymer resin (FEP) is used as an adhesive during the application of heat and pressure.

Stainless steel and other metal wires are employed as a guide wire for assisting in the insertion of a catheter; however, the large friction coefficient of metals causes difficulty in steering the guide wire to be smoothly inserted into the body and medical settings need an improvement in this steerability. A potentially promising technique is to coat the metal wire with PTFE of low friction coefficient; however, because of the various problems with this technique, e.g., inability of certain kinds of metal wires to be heated at high temperature, difficulty in applying a uniform coating to thin metal wires by this technique, and the aforementioned poor adhesion between PTFE and metals, the application of PTFE coating to metal wires has yet to be commercialized.

Patent Document 2 describes a guide wire having a lubricating layer that is formed of a hydrophilic polymeric substance that develops lubricating properties when it is wet.

In addition, Patent Document 3 describes a coated product comprising a material to be coated and a coating layer covering at least that portion of the material to be coated which is to be contacted with body fluid, the coating layer comprising at least fine particles of a fluorine-containing polymer and a non-fluorine-containing polymer.

Patent Document 1: JP 2004-181089 A
Patent Document 2: JP 2002-28249 A
Patent Document 3: WO 98/38258

DISCLOSURE OF THE INVENTION

Problems to be Solved by the Invention

As will be shown by the result of Reference Example 3 to be given later, coating with a mixed solution of PTFE (fluorine-containing polymer) and PVA (hydrophilic polymer) is such that as the mixing ratio of PTFE increases, the friction coefficient becomes lower to improve the slipperiness; however, the coated product described in Patent Document 3 is such that some of the fine particles of fluorine-containing polymer are simply exposed on the surface of the coating layer and the proportion of the fluorine-containing polymer on the surface is small; hence, compared to a coated product having an all-PTFE coating on its surface, the coated product of Patent Document 3 has low slipperiness.

Therefore, the present invention aims to solve the aforementioned problems of the prior art and provide a medical instrument in which the adhesion between a substrate and a fluorine-based thin film is improved to afford superior slipperiness.

Means to Solve the Problems

The present inventors found that the adhesion between a thin film of fluoropolymer such as PTFE and a substrate could be improved by interposing a specific thin film on the substrate.

The present invention provides the following specific inventions.
(1) A medical instrument comprising a substrate which is at least partially overlaid with a thin film of hydrophilic polymer which in turn is overlaid with a thin film of fluoropolymer.
(2) The medical instrument according to (1) above, wherein the thin film of fluoropolymer on top of the thin film of hydrophilic polymer is formed such that the substrate is at least partially coated with the thin film of hydrophilic polymer, which in turn is coated with a thin composite film of a hydrophilic polymer and a fluoropolymer, which in turn is coated with the thin film of fluoropolymer.
(3) The medical instrument according to (2) above, wherein the thin composite film has at least two layers of different compositions and is formed such that the ratio of the fluoropolymer to the hydrophilic polymer increases in steps from the hydrophilic polymer side towards the fluoropolymer side.
(4) The medical instrument according to any one of (1) to (3) above, wherein the hydrophilic polymer is a hydroxyl group-containing polymer and the fluoropolymer is polytetrafluoroethylene (PTFE).
(5) The medical instrument according to any one of (1) to (4) above, wherein at least one of the thin film of hydrophilic polymer, the thin film of fluoropolymer and the thin composite film is prepared by a wet process.
(6) The medical instrument according to any one of (1) to (4) above, wherein at least one of the thin film of hydrophilic polymer, the thin film of fluoropolymer and the thin composite film is prepared by a dry process.
(7) The medical instrument according to (6) above, wherein the dry process is vacuum evaporation.
(8) The medical instrument according to (6) above, wherein the dry process is sputtering.
(9) The medical instrument according to (6) above, wherein the dry process is evaporation polymerization.
(10) The medical instrument according to (6) above, wherein the dry process is plasma-enhanced CVD.
(11) The medical instrument according to any one of (1) to (10) above, wherein the substrate is made of a metal.
(12) The medical instrument according to any one of (1) to (10) above, wherein the substrate is made of plastics.
(13) The medical instrument according to (11) above, wherein the metal substrate is a metallic wire.

(14) The medical instrument according to (13) above, wherein the metallic wire is made of a nickel-titanium alloy or stainless steel.
(15) The medical instrument according to any one of (1) to (14) above, which is obtained by heating the substrate.
(16) The medical instrument according to (15) above, wherein the substrate is heated when forming at least one of the thin film of hydrophilic polymer, the thin film of fluoropolymer and the thin composite film.
(17) The medical instrument according to (15) or (16) above, wherein the substrate is heated such that at least one of the hydrophilic polymer and the fluoropolymer attains a temperature equal to or above its melting point or crystallization point.
(18) A process for producing the medical instrument according to any one of (1) to (14) above, which comprises the step of heating the substrate.
(19) The process according to (18) above, wherein the substrate is heated when forming at least one of the thin film of hydrophilic polymer, the thin film of fluoropolymer and the thin composite film.
(20) The process according to (18) or (19) above, wherein the substrate is heated such that at least one of the hydrophilic polymer and the fluoropolymer attains a temperature equal to or above its melting point or crystallization point.

Effects of the Invention

The medical instrument of the present invention has a thin film of fluoropolymer such as PTFE on the surface of a substrate, with its adhesion to the substrate being rendered high by interposing a specific thin film on the substrate. The resulting medial device is reduced in the friction coefficient of the substrate so that its slipperiness is improved whereas the device durability is enhanced. A variety of medical equipment that excels in thermal and chemical stability and friction characteristics (with slipperiness being particularly good) and which also excels in biocompatibility can be obtained by a simple manufacturing process.

Figure 1:
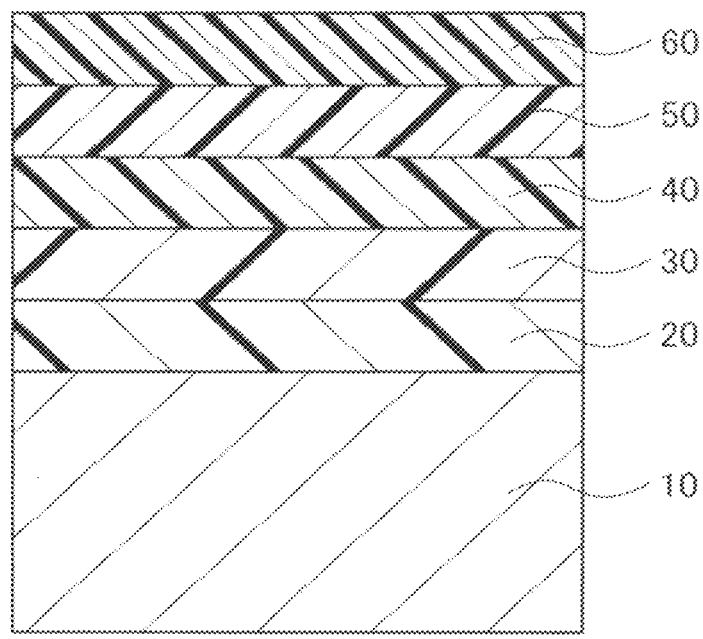
FIG. 1 is a sectional view showing an example of the structure in which thin films are stacked according to the present invention.

LEGEND 10 substrate
20 hydrophilic thin film
30 hydrophilic/fluorine-based composite thin film 1
40 hydrophilic/fluorine-based composite thin film 2
50 hydrophilic/fluorine-based composite thin film 3
60 fluorine-based thin film
110 nickel-titanium alloy substrate
120 EVOH/PTFE composite thin film
130 fine EVOH particle

BEST MODE FOR CARRYING OUT THE INVENTION

The medical instrument of the present invention comprises a substrate which is at least partially covered with a thin film of hydrophilic polymer which in turn is overlaid with a thin film of fluoropolymer.

When coating the substrate with a thin PTFE film, direct coating of the substrate with the thin PTFE film has had a problem with adhesion and no practical performance has been attainable unless the adhesion between the thin polymer film and the substrate material is improved. In the present invention, it has been found that if a thin film of hydrophilic polymer is interposed between the thin PTFE film and the substrate, the adhesion between the thin film of a fluoropolymer such as PTFE and the substrate is improved; this finding has led to the accomplishment of the present invention. In addition, the medical instrument of the present invention which has the thin fluoropolymer film on its surface excels in slipperiness in comparison with the coated product described in Patent Document 3 which has a fluoropolymer in only part of its surface.

The thin film of hydrophilic polymer to be used in the present invention is made of hydrophilic resins including, for example, cellulosic polymeric substances, polyethylene oxide-based polymeric substances, maleic anhydride-based polymeric substances (e.g. maleic anhydride copolymers such as methyl vinyl ether/maleic anhydride copolymer), acrylamide-based polymeric substances (e.g. polyacrylamide, and polyglycidyl methacrylate/dimethyl acrylamide (PGMA/DMAA) block copolymer), water-soluble nylon, polyvinyl alcohol, ethylene vinyl alcohol, and polyvinylpyrrolidone.

Resins having hydroxyl groups such as polyvinyl alcohol (PVA) and ethylene vinyl alcohol (EVOH) are used with advantage. It is also possible to use resins having hydrophilic functional groups such as carboxyl group, amino group, carbonyl group, and sulfo group.

The thin film of hydrophilic polymer is not particularly limited in thickness but if it is too thin, uniform coating is impossible whereas unduly great thickness is not economical; mostly because of these reasons, the thickness of that hydrophilic polymer film is preferably from 0.01 to 100 µm, more preferably from about 0.1 to about 10 µm, and even more preferably from 0.1 to 1 µm.

The thin film of hydrophilic polymer may comprise only one resin or two or more resins in a single layer or, alternatively, two or more layers of different resins may be combined into a thin composite film.

The medical instrument of the present invention has a thin fluoropolymer film on top of the above-described thin film of hydrophilic polymer. The thin fluoropolymer film may contain a wide variety of resins, such as fluorine-substituted epoxy resins, that have the hydrogen in the polymer replaced by fluorine. Preferred examples include: tetrafluororesins such as polytetrafluoroethylene (PTFE), tetrafluoroethylene/perfluoroalkyl vinyl ether copolymer (PFA), tetrafluoroethylene/hexafluoropropylene copolymer (FEP), and tetrafluoroethylene/ethylene polymer (ETFE); trifluororesins such as polychlorotrifluoroethylene (PCTTE) and chlorotrifluoroethylene/ethylene copolymer (ECTFE); difluororesins such as polyvinylidene fluoride (PVDF); and monofluororesins such as polyvinyl fluoride (PVF); mixtures of these resins may be used, as exemplified by an ETFE/PTFE composition. Polytetrafluoroethylene (PTFE) is preferred.

Fluoropolymers having those structures at selected sites can also be used.

If an even higher degree of adhesion is desired, the medical instrument preferably has a thin composite film between the thin film of hydrophilic polymer and the thin film of fluoropolymer, the composite film comprising a combination of the two polymers. The thin composite film preferably employs resins that are the same as the fluoropolymer and the hydrophilic polymer that are respectively used in the thin film of hydrophilic polymer and the thin film of fluoropolymer; if desired, other types of resins may be employed. It should however be noted that the mixing ratio between the fluoropolymer and the hydrophilic polymer is preferably adjusted in such a way that the compositional ratio changes in steps from the thin film of fluoropolymer towards the thin film of hydrophilic polymer.

For example, as illustrated in section in FIG. 1, a thin PVA film layer 20 is formed on a substrate 10 and overlaid with a thin PVA/PTFE composite film layer 30 (PVA:PTFE=2:1 (mass ratio)) which in turn is overlaid with a thin PVA/PTFE composite film layer 40 (PVA:PTFE=1:1 (mass ratio)) which in turn is overlaid with a thin PVA/PTFE composite film layer 50 (PVA:PTFE=1:2 (mass ratio)), which in turn is overlaid with a thin PTFE film layer 60.

The term mass ratio as used herein means the weight ratio between a solution having PVA dissolved in distilled water at a concentration of 8% (w/w) and a solution having PTFE dispersed in aqueous solution at a concentration of 60% (w/w).

The thin film of fluoropolymer is not particularly limited in thickness but if it is too thin, uniform coating is impossible whereas unduly great thickness is not economical; mostly because of these reasons, the thickness of that fluoropolymer film is preferably from 0.01 to 100 μm, more preferably from about 0.1 to about 10 μm.

The substrate is not limited and may be exemplified by polymeric materials such as plastics, and inorganic materials such as metals and ceramics.

Plastics include, but are not limited to, soft polyvinyl chloride (PVC), hard polyvinyl chloride, polypropylene (PP), polyethylene (PE), polyethylene terephthalate (PET), silicone resins, polyamides such as nylon, polymethyl methacrylate (PMMA), polyurethane (PU), polycarbonates, and thermoplastic elastomers (TPE).

The metal substrate can be made of various materials including nickel, titanium, and stainless steel, as well as copper, aluminum, and iron. It can also be exemplified by super-elastic alloys such as Ni—Ti based alloys, cobalt-based alloys such as Co—Ni—Cr based alloys, and other alloys.

The shape of the substrate may be of any shapes including a flat sheet, a rod, a thread, and three-dimensional shapes; in the present invention, metal substrates in the form of an elongated wire with a diameter of about 0.1-10 mm are particularly preferred. Coating methods (A) and (B) to be explained later are particularly effective.

The medical instrument is not limited but medical instruments for use in the living body are preferred, as exemplified by artificial organs, stents, catheters, guide wires, orthopedic materials (e.g. implants), medical patches, and sutures; all medical instruments that comprise a substrate which is at least partially covered with a thin film of hydrophilic polymer which in turn is overlaid with a thin film of fluoropolymer are included within the category of the medical instrument of the present invention.

The methods of forming the thin hydrophilic polymer film, the thin fluoropolymer film and the thin composite film of the present invention are not limited. The thin films may all or partly be formed by stacking resin films or by compressing, extruding or otherwise shaping particles and then firing the shaped powder; a preferred method is coating the thin PTFE film by (A) a dry process such as vacuum evaporation, evaporation polymerization, sputtering or plasma-enhanced CVD or (B) a wet process which comprises applying a solution of fine PTFE particles. In the dry process, PTFE as the starting material for coating need not be dissolved in a solvent or the like but can be used as such and yet a uniform coating film can be formed. The wet process, which does not use vacuum processing, has not only convenience in the process of film deposition but also the advantage of being fast in film deposition.

Heating the substrate during manufacturing the medical material of the present invention is preferred since it contributes to improving the adhesion to the substrate, thereby proving more effective.

The effectiveness of heating the substrate for the purpose of providing better adhesion is also recognized if it is heated when forming the thin hydrophilic polymer or fluoropolymer film and particularly great effect is obtained if it is heated when forming the thin composite film of hydrophilic polymer and fluoropolymer.

The reason why superior adhesion is obtained by heating the substrate when forming the thin composite film is explained below.

The thin composite film formed by a plasma-assisted method such as sputtering or plasma-enhanced CVD depends on molecular or atomic reactions for film formation and, hence, the hydrophilic polymer and the fluoropolymer form chemical bonds and will not experience phase separation. On the other hand, the thin composite film formed by the wet process or a non-plasma-assisted method such as vacuum evaporation may sometimes experience phase separation between the hydrophilic polymer and the fluoropolymer. To be more specific, masses of the fluoropolymer may occur as fine particles within the hydrophilic polymer or masses of the hydrophilic polymer may occur within the fluoropolymer. A thin composite film undergoing such phase separation is poor in the adhesion to the substrate. However, if the substrate is heated when forming the thin composite film, the dispersion of fine particles is suppressed and the adhesion to the substrate can eventually be improved.

Heating of the substrate may be effected after forming the above-mentioned thin films but it is preferably done when at least one thin film selected from among the above-mentioned thin hydrophilic polymer film, thin fluoropolymer film and thin composite film is formed. In particular, as mentioned above, heating the substrate when forming the thin composite film is more preferred since it provides greater effectiveness in improving the adhesion.

Heating of the substrate is preferably performed in such a way that at least one of the hydrophilic polymer and the fluoropolymer mentioned above attains a temperature equal to or above its melting point or crystallization point because this provides great effectiveness in improving the adhesion. In particular, it is more preferred to perform heating of the substrate such as to attain a temperature equal to or above the melting point or crystallization point of the hydrophilic polymer.

It should, however, be noted that if the heating temperature is unduly high, the thin composite film is charred, so it is usually preferred to heat the substrate such that the temperature of its surface is 500° C. or below, more preferably 350° C. or below. In addition, from the viewpoint of the characteristics of the substrate, the heating temperature is preferably such that the mechanical characteristics (such as flexural rigidity) of the substrate will not be changed. It is preferred that the mechanical characteristics of the substrate before heating be substantially maintained after heating. For example, in the case of an Ni—Ti based alloy, the substrate is preferably heated to 200° C. or below although the exact temperature depends on the time and method of treatment.

Hereinafter, the above-mentioned process (A) will be explained in greater detail with reference to an exemplary case where PTFE is used as the fluoropolymer and EVOH as the hydrophilic polymer, and the above-mentioned process (B) with reference to an exemplary case where PTFE is used as the fluoropolymer and PVA as the hydrophilic polymer.

The above-mentioned process (A) is first described with reference to the case of forming the above-mentioned thin films on the substrate by vacuum evaporation through resistance heating. Pellets of EVOH resin (such as those manufactured by KURARAY CO., LTD.) are charged into a crucible, which is supplied with a voltage and heated up to a predetermined temperature, whereupon the EVOH vapor is generated and a thin film is formed on the substrate. Subsequently, a PTFE sheet (such as the one manufactured by Hakudo Co., Ltd.) that has been crushed into pellets of about 3 mm square is charged into a crucible, which is supplied with a voltage and heated up to a predetermined temperature, whereupon the PTFE vapor is generated and a thin PTFE film is formed on the thin EVOH film.

If there is an additional need to improve the adhesion between the substrate and the thin PTFE film, a thin composite film of EVOH and PTFE is formed after forming the aforementioned thin EVOH film on the substrate. The thin composite film could be formed by charging the pellets of EVOH and PTFE resins into the same crucible and performing film deposition; however, in order to control the resin composition, the respective resins may be charged into different crucibles, which are supplied with a voltage and heated to predetermined temperatures, whereupon vapors are generated and a thin film is formed on the substrate. In this case, it is recommended to install a mechanism for rotating the substrate such that no distribution will occur in the composition of the thin film on the substrate. While the composition of the thin composite film may be controlled by such factors as the shape of the respective crucibles, the rate of film deposition can be controlled by controlling the temperature in the crucibles, so it is recommended to perform the control using a system that monitors the temperature in the crucibles, as exemplified by a thermocouple. The thin composite film layer may be a single layer but from the viewpoint of improving the adhesion, it is preferred to change the resin composition in steps as depicted in FIG. 1.

Next, the above-described method of heating the substrate is explained in greater detail.

The method of heating the substrate is not limited in any particular way but if the aforementioned thin composite film of EVOH and PTFE is to be formed, heating of the substrate is preferably done using a heater that is capable of temperature control.

The heating temperature and method depend on the material and shape of the substrate and an optimum method varies with these factors; if the substrate is like a metal sheet, an exemplary preferred method is by installing a heater in plate form between a substrate holder and the substrate and heating the substrate from its back side. If the substrate is linear (such as a wire), an exemplary preferred method is either by causing an electric current to pass through the wire so that the substrate is heated by the resistance of the wire or by using a heater in plate form as in the aforementioned case where the substrate is like a sheet.

As mentioned above, the temperature for heating the substrate is preferably such that it is heated until the hydrophilic polymer and fluoropolymer at least attain a temperature equal to or above the melting point or crystallization point of either one of them because this contributes to improving the adhesion to the substrate.

Specifically, in the case of forming a thin composite film of PTFE and EVOH, the temperature for heating the substrate is adjusted to about 200-300° C., preferably about 230-270° C., and this contributes to better adhesion. If the aforementioned thin composite film is deposited with the substrate temperature being controlled to lie between room temperature and about 150° C., fine particles as masses of evaporated particles will appear on the surface of the thin composite film but if film deposition is performed with the substrate being heated within the aforementioned temperature range, the above-mentioned fine particles will disappear and the adhesion to the substrate is eventually improved.

The above-mentioned fine particles are presumably the fine particles of EVOH in view of the surface morphology of thin films that are individually deposited from PTFE and EVOH and it is generally held that fine particles will not disappear unless they are heated to more than the melting point of whichever the polymer that has the higher heat resistance. To be more specific, since PTFE is more heat resistant (has a higher melting point) than EVOH, it is held that fine particles will not disappear unless they are heated to more than the melting point of PTFE (326° C.). However, the present inventors found that upon heating to more than the melting point of EVOH, fine particles did not appear on the surface of the thin composite film, thus giving better adhesion. This would be because the evaporated particles have a certain amount of energy and they are so small as to exhibit high efficiency of heat conduction.

Described next is the case of forming the abovementioned thin films on the substrate by RF sputtering. Pellets of EVOH resin (such as those manufactured by KURARAY CO., LTD.) are heated to melt and a sheet is molded for use as a target in film deposition. For deposition of a thin PTFE film, a PTFE sheet (such as the one manufactured by Hakudo Co., Ltd.) may be used as a target. As in the case of vacuum evaporation, a thin EVOH film is first formed on the substrate and thereafter a thin PTFE film is formed. If there is an additional need to improve the adhesion between the substrate and the thin PTFE film, a thin composite film of EVOH and PTFE is formed after forming the aforementioned thin EVOH film on the substrate. To form the thin composite film, targets for EVOH and PTFE are separately prepared and simultaneous film deposition is performed. By controlling the input powers independently of each other, the rate of film deposition is controlled, which in turn allows the composition of the thin composite film to be controlled. If just one type of target is used to deposit the thin composite film, the desired control is possible by changing the area of the target.

In the case of RF sputtering, the thin composite film layer may be a single layer but, again as in the aforementioned case of vacuum evaporation, from the viewpoint of improving the adhesion, it is preferred to change the resin composition in steps as depicted in FIG. 1.

Hereinafter, the case of forming a thin PVA film and a thin PTFE film on the substrate by the above-mentioned wet process (B) is described.

A PVA resin (such as the one manufactured by KURARAY CO., LTD.) is dissolved in distilled water and the solution is sprayed over the substrate. In order to enhance the film uniformity, it is recommended to deposit a PVA film on the rotating substrate. After it is applied, PVA is solidified with a dryer to form a thin PVA film on the substrate. The thin PVA film is coated with a PTFE solution (e.g. POLYFLON™

PTFE of DAIKIN INDUSTRIES, Ltd.) and PTFE is solidified with a dryer to form a thin PTFE film. If, as in the case of the aforementioned process (A), there is a need to improve the adhesion between the substrate and the thin PTFE film, a thin composite film of PVA and PTFE is formed after forming the aforementioned thin PVA film on the substrate.

The thin composite film may be formed by a process comprising mixing the aforementioned PVA and PTFE solutions, applying the mixed solution onto the thin PVA film, and solidifying the applied resins with a dryer to form a thin PVA-PTFE composite film. As in the aforementioned process (A), the thin composite film layer may be a single layer but from the viewpoint of improving the adhesion, it is preferred to change the resin composition in steps as depicted in FIG. 1. To change the resin composition, one may simply change the mixing ratio between the PVA and PTFE solutions.

Hereinabove, the present invention has been specifically exemplified by referring to vacuum evaporation and RF sputtering as examples of the dry process (A), as well as to the wet process (B) but it goes without saying that the individual thin films mentioned above can be formed by whichever preferred of the processes (A) and (B). For example, the wet process may be combined with the dry process, as exemplified by the case where the thin hydrophilic polymer film is formed by the wet process involving the application of a resin solution and the thin PTFE film is formed by the dry process. Needless to say, the wet process (B) may be used to form the hydrophilic polymer layer or thin composite film layer whereas vacuum evaporation or RF sputtering as process (A) may be used to form the fluoropolymer layer. If desired, the hydrophilic polymer layer, thin composite film layer and the fluoropolymer layer may be formed by the wet process (B), with the fluoropolymer layer being then overlaid with another fluoropolymer layer by the dry process (A).

The method of measuring the friction and adhesion of a thin film coated on a metal substrate may be exemplified by the following methods, which of course are not the sole examples.

1) In the Case where the Substrate is Like a Flat Sheet

For a scratch test on the thin film, a pin-on-disk friction and wear tester (such as the evaluation equipment described in "Materials Science and Technology", Journal of the Materials Science Society of Japan, vol. 41, p. 326 (2004)) is used. The disk is adjusted to rotate at 5 rpm with a radius of 4 mm; in the case of measuring the friction coefficient of the thin film, a load of 20 g is applied and in the case of measuring the durability of the thin film, a load of 100 g is applied.

2) In the Case where the Substrate is Like a Rod

When the substrate is like a rod (wire), it is scratched in two-dimensional (reciprocating) directions and the same procedure as 1) above may be followed.

3) In the Case where the Substrate is in a Three-Dimensional Shape (Other than Like a Flat Sheet and a Rod)

When the substrate is in a three-dimensional shape, part of it is sampled and the same method as 1) or 2) may be used for evaluation.

The thin film is evaluated for adhesion by determining the degree of peeling of the thin film from the substrate. The principle is: when the thin film separates, an electric current flows between the pin and the metal substrate, so the degree of peeling can be determined by counting the number of points where the electric current flows while the pin circulates on the disk (such as the evaluation equipment described in "Materials Science and Technology", Journal of the Materials Science Society of Japan, vol. 41, p. 326 (2004)). The larger the degree of peeling that occurs after the passage of a specified time, the lower will be the adhesion of the thin film. The result of direct measurement of the adhesion between the substrate and the thin film by a pull test (e.g. the evaluation equipment described in Technology Research Report, The Institute of Electronics, Information and Communication Engineers, OME 2004-96, p. 25 (2004)) has been found to have a certain correlation with the result of the peel test described above, so the latter may as well be considered to be an appropriate method for evaluating the adhesion.

EXAMPLES

Hereinafter, the present invention is described in greater detail by reference to examples. The present invention is by no means limited to those examples.

Example 1

By vacuum evaporation through resistance heating, a thin EVOH film was deposited to a thickness of 0.1 μm around a SUS 302 wire (10 cm long and 0.35 mm in diameter) and then a thin composite film of EVOH and PTFE (with a film thickness of 0.1 μm) was formed. The rate of film deposition was controlled by adjusting the temperature in the crucible such that the compositional ratio between EVOH and PTFE in the thin composite film would be 1:1. The thin composite film was overlaid with a thin PTFE film to a thickness of 0.5 μm by vacuum evaporation, again through resistance heating. The thus prepared sample was designated J-1.

Example 2

By RF sputtering, a thin EVOH film was deposited to a thickness of 0.2 μm on a nickel-titanium alloy sheet (50 mm×50 mm×2 mm thick) and it was then overlaid with a thin PTFE film to a thickness of 1 μm, again by RF sputtering. The thus prepared sample was designated J-2.

Example 3

By RF sputtering, a thin EVOH film was deposited to a thickness of 0.2 μm around a nickel-titanium alloy wire (10 cm long and 0.35 mm in diameter) and it was then overlaid with a thin PTFE film to a thickness of 5 μm, again by RF sputtering. The thus prepared sample was designated J-3.

Example 4

One part by mass of PVA (PVA-217 manufactured by KURARAY, CO., LTD.) was dissolved in 99 parts by mass of water to prepare a PVA solution. Liquid mixtures of the PVA solution and a PTFE solution (POLYFLON™ PTFE dispersion D-1E manufactured by DAIKIN INDUSTRIES, Ltd.) were prepared. The PVA solution mixed with the PTFE solution at 2:1 (by mass ratio) was designated liquid mixture 1; the mixture at 1:1 (by mass ratio) was designated liquid mixture 2; and the mixture at 1:2 (by mass ratio) was designated liquid mixture 3. The PVA solution was first applied around each of a SUS 302 wire (10 cm long and 0.35 mm in diameter) and a nickel-titanium alloy wire (10 cm long and 0.25 mm in diameter). To enhance the film uniformity, each of the SUS 302 wire and the nickel-titanium alloy wire was rotated during film deposition. After applying the PVA, heating was effected with a dryer at 100° C. for 15 minutes to solidify the PVA, whereupon a thin PVA film was formed around each of those metal wires in FIG. 1). Subsequently, liquid mixture 1 was applied and heated with a dryer at 180° C. for 15 minutes to solidify in FIG. 1) and, thereafter, liquid mixture 2 was applied and heated with a dryer at 180° C. for 15 minutes to solidify (40 in FIG. 1). The solidified layer in turn was coated with liquid mixture 3 and the applied coating was heated with a dryer at 180° C. for 15 minutes to solidify (50 in FIG. 1); thereafter, the solidified coating in turn was overlaid with the PTFE solution and the applied coating was heated with a dryer at 180° C. for 15 minutes to solidify, thereby forming a thin PTFE film (60 in FIG. 1). Each of layers 20, 30, 40 and 50 in FIG. 1 was 0.5 μm thick whereas composite film 60 had a thickness of 2 μm. The thus prepared samples were respectively designated J-4A and J-4B.

Reference Example 1

By vacuum evaporation through resistance heating, a thin composite film (120 in FIG. 3) was formed to a thickness of 1 μm on a nickel-titanium alloy sheet (50 mm×50 mm×2 μm thick, 110 in FIG. 3) held at room temperature, with the temperature in the crucible being controlled such that the ratio between EVOH and PTFE would be 1:4; the thus prepared sample was designated R-5.

Reference Example 2

A thin composite film was formed to a thickness of 1 μm by adjusting the temperature in the crucible such that the ratio between EVOH and PTFE would be 1:4 as in Reference Example 1, except that a heater was installed on the back side of the substrate which was heated until the temperature of its surface reached 250° C.; the thus prepared sample was designated T-5.

Figure 2:
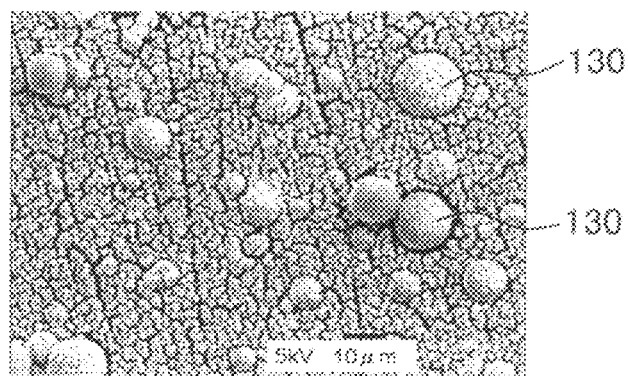
FIG. 2 is an electron micrograph showing the surface of a PTFE/EVOH composite thin film (sample R-5) prepared according to the present invention.
Figure 3A:
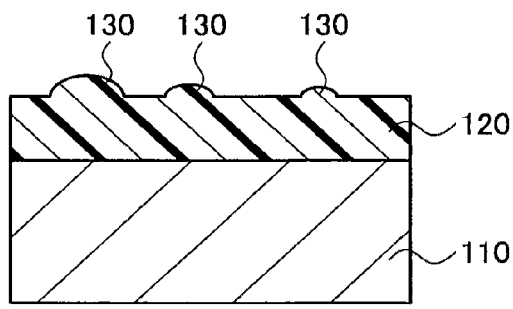
FIGS. 3A-3B shows in schematic section PTFE/EVOH composite thin films prepared according to the present invention; (A) refers to the sample (R-5) prepared by film deposition at room temperature, and (B) refers to the sample (T-5) prepared by film deposition at a substrate temperature of 250° C.
Figure 3B:
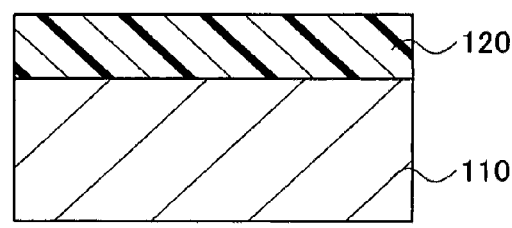

The surface state of each of the thin composite films in samples R-5 and T-5 was examined with an electron microscope. FIG. 2 is an electron micrograph of the surface of sample R-5 (Reference Example 1). FIG. 3(A) is a schematic cross section of sample R-5 whereas FIG. 3(B) is a schematic cross section of sample T-5 (Reference Example 2).

As FIG. 2 and FIG. 3(A) show, fine particles such as those found in the coated product described in the abovementioned Patent Document 3 were recognized (130 in FIG. 2 and FIG. 3) but none of such fine particles were recognized in sample T-5.

Examples 5 and 6

By vacuum evaporation through resistance heating, a thin EVOH film was deposited to a thickness of 0.1 μm on a nickel-titanium alloy sheet (50 mm×50 mm×2 μm thick) and then a thin composite film of EVOH and PTFE (with a film thickness of 0.1 μm) was formed. The rate of film deposition was controlled by adjusting the temperature in the crucible such that the compositional ratio between EVOH and PTFE in the thin composite film would be 1:4. The thin composite film was overlaid with a thin PTFE film to a thickness of 0.5 μm by vacuum evaporation, again through resistance heating.

The sample prepared by performing the series of these thin film forming steps at room temperature was designated J-5R (Example 5) and the sample prepared by the same procedure except that the substrate was heated at 250° C. was designated J-5T (Example 6).

Comparative Example 1

Only a thin PTFE film (0.7 μm thick) was formed around a SUS 302 wire (10 cm long and 0.35 mm in diameter) by the method shown in Example 1. Neither a thin EVOH film layer nor a thin EVOH-PTFE composite film layer was formed. The thus prepared sample was designated H-1.

Comparative Example 2

Only a thin PTFE film (1.2 μm thick) was formed on a nickel-titanium alloy sheet (50 mm×50 mm×2 μm thick) by the method shown in Example 2. Neither a thin EVOH film layer nor a thin EVOH-PTFE composite film layer was formed. The thus prepared sample was designated H-2.

Comparative Example 3

Only a thin PTFE film (5.2 μm thick) was formed around a nickel-titanium alloy wire (10 cm long and 0.35 mm in diameter) by the method shown in Example 3. Neither a thin EVOH film layer nor a thin EVOH-PTFE composite film layer was formed. The thus prepared sample was designated H-3.

Comparative Example 4

Only a thin PTFE film (8 μm thick) was applied around each of a SUS 302 wire (10 cm long and 0.35 mm in diameter) and a nickel-titanium alloy wire (10 cm long and 0.25 mm in diameter). To enhance the film uniformity, each of the SUS 302 wire and the nickel-titanium alloy wire was rotated during film deposition. After applying the PTFE solution, heating was effected with a dryer at 180° C. for 15 minutes to solidify the PTFE, whereupon a thin PTFE film was formed. Neither a thin PVA film layer nor a thin PVA-PTFE composite film layer was formed. The thus prepared samples were respectively designated H-4A and H-4B.

<Methods of Evaluation>

1) In the Case of a Substrate Like a Flat Sheet (in the Case of Samples J-2 and H-2)

For a scratch test on the thin film, a pin-on-disk friction and wear tester (such as the evaluation equipment described in "Materials Science and Technology", Journal of the Materials Science Society of Japan, vol. 41, p. 326 (2004)) was used. The disk was adjusted to rotate at 5 rpm with a radius of 4 mm. In the case of measuring the friction coefficient of the thin film, a load of 20 g was applied and in the case of measuring the durability of the thin film, a load of 100 g was applied.

2) In the Case where the Substrate was Like a Rod (in the Case of Samples Other than the Above)

When the metal substrate was like a rod (wire), it was scratched in reciprocating directions. Other conditions were the same as above.

3) The Thin Film was Evaluated for Adhesion by Determining the Degree of Peeling of the Thin Film from the Substrate. The principle was: when the thin film separates, an electric current flows between the pin and the metal substrate, so the degree of peeling can be determined by counting the number of points where the electric current flows while the pin circulates on the disk (while the pin reciprocates once in the case where the substrate is like a rod) (evaluation equipment described in "Materials Science and Technology", Journal of the Materials Science Society of Japan, vol. 41, p. 326 (2004)). The larger the degree of peeling that occurs after the passage of a specified time, the lower will be the adhesion of the thin film.

(Result of Evaluation of Friction Coefficients)

The friction coefficients of samples J-1 to J-4A, 4B, 5R and 5T were measured with the aforementioned pin-on-disk friction and wear tester and in all cases, the values were lower than the friction coefficients of the substrates, indicating good slipperiness.

(Evaluation of Adhesion 1)

Samples J-1 to J-4 and samples H-1 to H-4 were evaluated for adhesion by means of the aforementioned pin-on-disk friction and wear tester and the results of evaluation were summarized in Table 1. In Table 1, Good refers to non-occurrence of peel and Poor occurrence of peel (ND means "yet to be evaluated")

(Evaluation of Adhesion 2)

For samples R-5, T-5, J-5R and J-5T referred to in Example 5, the adhesion between the nickel-titanium alloy substrate and the thin film was directly measured by a pull test (e.g. the evaluation equipment described in Technology Research Report, The Institute of Electronics, Information and Communication Engineers, OME 2004-96, p. 25 (2004)) and the relative intensities with the adhesion strength of R-5 being taken as unity (i.e., how many times the strength of R-5) were shown in Table 2.

The results in Tables 1 and 2 verified the effectiveness of the present invention in terms of the adhesion between the metal substrate and the thin film. In particular, compared to J-5R which was prepared without heating of the substrate when forming the respective thin films, J-5T which involved such heating was surprisingly about three times as strong.

TABLE 1

Table 1 Results of Evaluation of Adhesion

|  | J-1 | H-1 | J-2 | H-2 | J-3 | H-3 | J-4A | H-4A | J-4B | H-4B |
|---|---|---|---|---|---|---|---|---|---|---|
| Adhesion after 10 reciprocations | Good | Poor | Good | Good | Good | Good | Good | Poor | Good | Poor |
| Adhesion after 30 reciprocations (rotations) | Poor | Poor | Good | Poor | Good | Poor | Good | Poor | Good | Poor |
| Adhesion after 300 reciprocations | Poor | Poor | ND | Poor | ND | Poor | Good | Poor | Good | Poor |

TABLE 2

Table 2 Results of Evaluation of Adhesion Strength by Pull Test

| Sample name | R-5 | T-5 | J-5R | J-5T |
|---|---|---|---|---|
| Adhesion strength | 1.0 | 2.1 | 1.1 | 3.4 |

Reference Example 3

Figure 4:
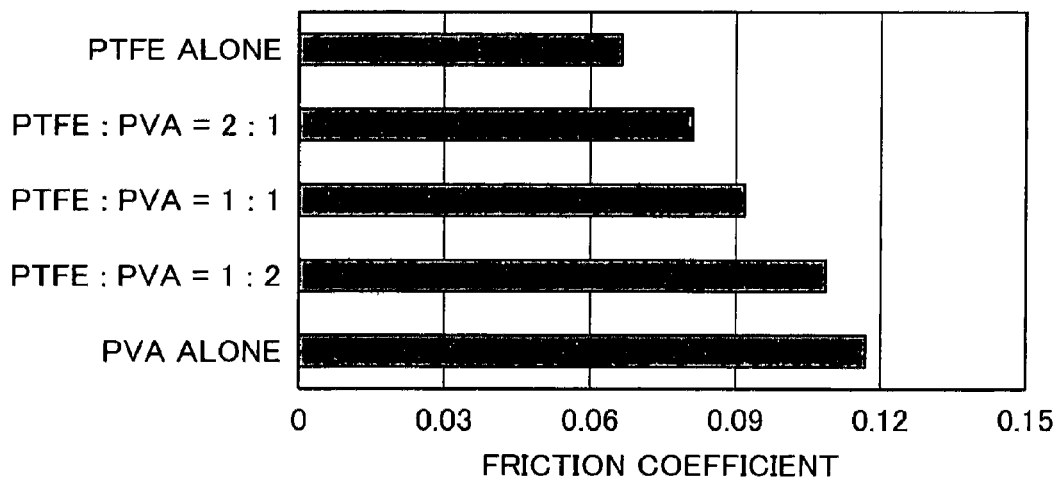
FIG. 4 is a graph showing the friction coefficients of the samples prepared in Reference Example 3.

Using a PTFE solution (PTFE dispersion, product of DAIKIN Ltd., PTFE contained in 60 mass %), a PVA solution (POVAL, product of KURARY CO., LTD., PVA contained in 8 mass %) or mixed solutions prepared by mixing those solutions in the mass ratios indicated in FIG. 4 were used and spin-coated to form thin films on Ni—Ti alloy substrates (60 mm in diameter and 1 mm thick), thereby preparing samples. The conditions for film deposition were: dripping in 0.5 ml, rotating at 1500 rpm, drying preliminarily at 100° C. for 30 minutes, and drying thoroughly at 180° C. for 30 minutes.

The friction coefficient of each sample was measured with the aforementioned pin-on-disk friction and wear tester.

As is clear from the result shown in FIG. 4, it was found that the thin PVA film had the highest friction coefficient whereas the thin PTFE film had the lowest friction coefficient. In the thin PTFE-PVA composite film, the friction coefficient decreased with the increasing proportion of PTFE.

INDUSTRIAL APPLICABILITY

The processes (A) and (B) of the present invention have a potential to be applied as techniques for coating a wide variety of medical materials with thin fluoropolymer films (techniques for coating any shapes of materials with thin fluoropolymer films).

The invention claimed is:

1. A medical instrument comprising a substrate which is at least partially overlaid with a film of hydrophilic polymer, which in turn is coated with a composite film of a hydrophilic polymer and a fluoropolymer, and which in turn is coated with a film of fluoropolymer, the composite film including a fluoropolymer side and an opposite hydrophilic polymer side, the fluoropolymer side of the composite film being closer to the film of fluoropolymer than the hydrophilic polymer side of the composite, the composite film comprising at least two layers of different compositions, and a ratio of the fluoropolymer to the hydrophilic polymer in the composite film increases in steps from the hydrophilic polymer side towards the fluoropolymer side.

2. The medical instrument according to claim 1, wherein the hydrophilic polymer is a hydroxyl group-containing polymer and the fluoropolymer is polytetrafluoroethylene (PTFE).

3. The medical instrument according to claim 1, wherein the substrate is made of a metal.

4. The medical instrument according to claim 3, wherein the metal substrate is a metallic wire.

5. The medical instrument according to claim 4, wherein the metallic wire is made of a nickel-titanium alloy or stainless steel.

6. The medical instrument according to claim 1, wherein the substrate is made of plastics.

7. A process for producing the medical instrument according to claim 1, which comprises the step of heating the substrate.

8. The process according to claim 7, wherein the substrate is heated when forming at least one of the film of hydrophilic polymer, the film of fluoropolymer and the composite film.

9. The process according to claim 7, wherein the substrate is heated such that at least one of the hydrophilic polymer and the fluoropolymer attains a temperature equal to or above its melting point or crystallization point.

10. A process for producing the medical instrument according to claim 1, further comprising preparing at least one of the film of hydrophilic polymer, the film of fluoropolymer and the composite film by a wet process.

11. A process for producing the medical instrument according to claim 1, further comprising preparing at least one of the film of hydrophilic polymer, the film of fluoropolymer and the composite film by a dry process.

12. A process for producing the medical instrument according to claim 11, wherein the dry process is vacuum evaporation, sputtering, or evaporation polymerization.

13. A process for producing a medical instrument comprising:
- coating a hydrophilic polymer on at least partially a substrate to form a film of the hydrophilic polymer;
- coating the film of the hydrophilic polymer with a hydrophilic polymer and a fluoropolymer to form a composite film of the hydrophilic polymer and the fluoropolymer on the hydrophilic polymer; and then
- coating the fluoropolymer on at least partially the composite film to form a film of the fluoropolymer,
- wherein the composite film has at least two layers of different compositions and is formed such that a ratio of the hydrophilic polymer and the fluoropolymer increases in steps from a hydrophilic polymer side of the composite film towards a fluoropolymer side of the composite film.

14. The process according to claim 13, further comprising:
- heating the substrate when coating at least one of the film of the hydrophilic polymer, the composite film and the film of the fluoropolymer.

15. The process according to claim 14, further comprising:
- the heating of the substrate comprising heating so that at least one of hydrophilic polymer and the fluoropolymer attains a temperature equal to or above its melting point or crystallization point.

16. A process for producing a medical instrument comprising:
- coating a hydrophilic polymer on at least partially a substrate to form a film of the hydrophilic polymer;
- coating a fluoropolymer on at least partially the film of the hydrophilic polymer to form a film of the fluoropolymer, and
- heating the substrate when coating the film of the fluoropolymer, the heating of the substrate comprising heating so that the fluoropolymer attains a temperature equal to or above its melting point or crystallization point.

17. A process for producing a medical instrument comprising:
- coating a hydrophilic polymer on at least partially a substrate to form a film of the hydrophilic polymer;
- coating the film of the hydrophilic polymer with a hydrophilic polymer and a fluoropolymer to form a composite film of the hydrophilic polymer and the fluoropolymer on the hydrophilic polymer; and then
- coating the fluoropolymer on at least partially the composite film to form a film of the fluoropolymer, and
- heating the substrate when coating the composite film, the heating of the substrate comprising heating so that the polymers comprising the composite film attain a temperature equal to or above their melting point or crystallization point.

* * * * *